(12) United States Patent
Sun et al.

(10) Patent No.: US 10,168,219 B2
(45) Date of Patent: Jan. 1, 2019

(54) WEARABLE DEVICE WITH COMBINED SENSING CAPABILITIES

(71) Applicants:Chih-Ming Sun, HsinChu (TW); Ming-Han Tsai, HsinChu (TW)

(72) Inventors: Chih-Ming Sun, HsinChu (TW); Ming-Han Tsai, HsinChu (TW)

(73) Assignee: PIXART IMAGING INCORPORATION, Hsinchu (TW)

( * ) Notice: Subject to any disclaimer, the term of this patent is extended or adjusted under 35 U.S.C. 154(b) by 744 days.

(21) Appl. No.: 14/726,472

(22) Filed: May 30, 2015

(65) Prior Publication Data

US 2016/0273967 A1 Sep. 22, 2016

(30) Foreign Application Priority Data

Mar. 20, 2015 (TW) .............................. 104108897 A (51) Int. Cl.
*G01J 5/02* (2006.01)
*B81B 7/02* (2006.01)
(Continued)

(52) U.S. Cl.
CPC .......... *G01J 5/0265* (2013.01); *B81B 7/0025* (2013.01); *B81B 7/0061* (2013.01); *B81B 7/02* (2013.01);
(Continued)

(58) Field of Classification Search
CPC ............ G01K 7/02; G01K 3/005; G01K 3/10; G01K 7/42; G01K 7/22; G01K 13/02; G01K 2205/04; G01K 2013/024; G01K 7/16; G01K 7/01; G01K 7/10; G01K 11/32; G01K 13/00; B23K 31/02; G01F 1/00; G01N 25/72; G01N 25/28; G01N 25/32; G01N 33/225; G01N 33/02; H05K 7/20945; F24F 11/0012; F24F 2001/0052; F24F 2011/0093; F24F 11/022; H02M 1/32;
(Continued)

(56) References Cited

U.S. PATENT DOCUMENTS 5,430,692 A 7/1995 Grupp et al.
5,907,282 A * 5/1999 Tuorto .................. G08B 21/06
340/439
(Continued)

FOREIGN PATENT DOCUMENTS

JP 2007271413 A * 10/2007 ................ G01J 5/04

*Primary Examiner* — Manish S Shah
(74) *Attorney, Agent, or Firm* — Tung & Associates (57) ABSTRACT

The present invention discloses a wearable device with combined sensing capabilities, which includes a wearable assembly and at least one multi-function sensor module. The wearable assembly is suitable to be worn on a part of a user's body. The wearable assembly includes at least one light-transmissible window. The multi-function sensor module is located inside the wearable assembly, for performing an image sensing function and an infrared temperature sensing function. The multi-function sensor module includes an image sensor module for sensing a physical or a biological feature of an object through the light-transmissible window by way of image sensing; and an infrared temperature sensor module for sensing temperature through the light-transmissible window by way of infrared temperature sensing.

3 Claims, 9 Drawing Sheets

(51) Int. Cl.
*H04N 5/225* (2006.01)
*B81B 7/00* (2006.01)

(52) U.S. Cl.
CPC ............ *G01J 5/027* (2013.01); *H04N 5/2256* (2013.01); *B81B 2201/0214* (2013.01); *B81B 2201/0235* (2013.01); *B81B 2201/0242* (2013.01); *B81B 2201/0278* (2013.01); *H01L 2224/48091* (2013.01); *H01L 2924/16151* (2013.01); *H01L 2924/16153* (2013.01); *H01L 2924/16235* (2013.01)

(58) Field of Classification Search
CPC .... H02M 1/38; H02M 1/53806; H01C 7/008; H01C 17/00; H01R 4/023; H01R 4/029; H01R 43/28; G01R 31/2642; G01R 31/048; G01R 31/40; G01J 5/004; G01J 5/00; G01J 5/003; G01J 5/043; G01J 5/0821; A47J 43/287; F16B 2/02; F16B 1/00; F16B 47/00; F16B 2001/0035; F16M 13/02; F16M 13/022
See application file for complete search history.

(56) References Cited

U.S. PATENT DOCUMENTS

| | | | |
|---|---|---|---|
| 6,425,688 B1 | 7/2002 | Hsu | |
| 7,894,869 B2* | 2/2011 | Hoarau | A61B 5/14552 600/323 |
| 8,092,393 B1* | 1/2012 | Rulkov | A61B 5/02438 600/301 |
| 8,140,143 B2 | 3/2012 | Picard et al. | |
| 2005/0070773 A1* | 3/2005 | Chin | A61B 5/14552 600/322 |
| 2007/0073117 A1* | 3/2007 | Raridan, Jr. | A61B 5/14552 600/310 |
| 2008/0267254 A1 | 10/2008 | Hsieh | |
| 2010/0160797 A1* | 6/2010 | Banet | A61B 5/02125 600/485 |
| 2011/0265706 A1 | 11/2011 | Nicholls | |
| 2014/0276244 A1* | 9/2014 | Kamyar | A61B 5/1112 600/595 |
| 2015/0340351 A1 | 11/2015 | Rossi et al. | |
| 2016/0073954 A1 | 3/2016 | Meitav | |

* cited by examiner

WEARABLE DEVICE WITH COMBINED SENSING CAPABILITIES

CROSS REFERENCE

The present invention claims priority to TW 104108897, filed on Mar. 20, 2015.

BACKGROUND OF THE INVENTION

Field of Invention

The present invention relates to a wearable device; particularly, it relates to a wearable device with combined sensing capabilities, in which an infrared temperature sensor is integrated.

Description of Related Art

U.S. Patent Publication No. 2011/0265706 discloses a wearable device for measuring an ambient environmental temperature or a surface temperature of an object. There are other prior arts disclosing a wearable devices for sensing blood pressure or heart rate. For reference, U.S. Pat. Nos. 8,140,143 and 5,430,692 are pertinent prior arts.

These prior arts, nevertheless, are only capable of performing one single sensing function, not multiple sensing functions. For example, there is no prior art integrating a heart rate sensing function, a temperature sensing function, a blood pressure meter and the relevant sensing circuits. None of these prior arts can sense, for example, both heart rate and temperature.

In view of the above, to overcome the drawbacks in the prior arts, the present invention proposes a wearable device with combined sensing capabilities, in which an infrared temperature sensor is integrated.

SUMMARY OF THE INVENTION

From one perspective, the present invention provides a wearable device with combined sensing capabilities, comprising: a wearable assembly for being worn on a part of a user's body, wherein the wearable assembly has at least one light-transmissible window; and at least one multi-function sensor module located inside the wearable assembly, for performing an image sensing function and an infrared temperature sensing function, the multi-function sensor module including: an image sensor module for sensing a physical or a biological feature of an object through the at least one light-transmissible window by way of image sensing; and an infrared temperature sensor module for sensing temperature through the at least one light-transmissible window by way of infrared temperature sensing.

In one embodiment, the image sensor module is for sensing heart rate, blood oxygen concentration, blood pressure or breathing rate.

In one embodiment, the multi-function sensor module further includes a substrate, a cap and at least one partitioning member, the cap covering a part of the substrate and the at least one partitioning member being on the substrate, to form at least two chambers for accommodating the image sensor module and the infrared temperature sensor module, respectively, wherein each of the at least two chambers has a light-transmissible zone, and a light beam is allowed to transmit between the light-transmissible zone and the light-transmissible window of the wearable assembly.

In one embodiment, the image sensor module includes a light source and an image sensor, the cap covering a part of the substrate and the at least one partitioning member being on the substrate, to form at least three chambers for accommodating the light source, the image sensor and the infrared temperature sensor module, respectively, wherein each of the at least three chambers has a light-transmissible zone, and a light beam is allowed to transmit between the light-transmissible zone and the light-transmissible window of the wearable assembly.

In one embodiment, the image sensor module includes a light source and an image sensor, the image sensor and the infrared temperature sensor module being integrated as one single module.

In one embodiment, the multi-function sensor module further includes a substrate, a cap covering a part of the substrate and at least one partitioning member, the cap and the at least one partitioning member being on the substrate, to form at least two chambers for accommodating the light source and the single module, respectively, wherein each of the at least two chambers has a light-transmissible zone, and a light beam is allowed to transmit between the light-transmissible zone and the light-transmissible window of the wearable assembly.

In one embodiment, the light source, the image sensor and the infrared temperature sensor module are not covered with a filler material.

In one embodiment, each of the light source and the image sensor is fully covered with or at least partially covered with a corresponding filler material, while the infrared temperature sensor module is not covered with a filler material.

In one embodiment, the light source, each of the light source, the image sensor and the infrared temperature sensor module is fully covered with or at least partially covered with a corresponding filler material.

In one embodiment, the light-transmissible zone corresponding to the infrared temperature sensor module is sealed entirely or partially with a light filtering material.

In one embodiment, a protection cap layer is connected above the infrared temperature sensor module, wherein a space between the protection cap layer and the infrared temperature sensor module is not filled with any filler material.

In one embodiment, a protection ring is provided between the infrared temperature sensor module and the light-transmissible zone corresponding to the infrared temperature sensor module, the protection ring surrounding a lateral periphery of a space between the infrared temperature sensor module and the corresponding light-transmissible zone.

In one embodiment, the multi-function sensor module further includes a micro-electro-mechanical systems (MEMS) device for providing one of the following functions: a sweat sensor, an ultraviolet light sensor, a gas sensor, an accelerometer, a gyroscope, an altimeter or a pedometer.

In one embodiment, the light-transmissible window is at an upper surface, a lower surface or a lateral surface of the wearable assembly.

In one embodiment, the wearable assembly has a light-transmissible window at an upper surface of the wearable assembly and another light-transmissible window at a lower surface of the wearable assembly, and the multi-function sensor module further includes a contact type temperature sensor, for sensing temperature through the two light-transmissible windows at the upper surface and the lower surface of the wearable assembly.

In one embodiment, the multi-function sensor module includes a temperature contact point located at the lower surface, for directly contacting the object, the temperature contact point being coupled to the contact type temperature sensor.

In one embodiment, the wearable assembly has a light-transmissible window at an upper surface of the wearable assembly and another light-transmissible window at a lower surface of the wearable assembly, and the infrared temperature sensor module senses temperature through the two light-transmissible windows at the upper surface and the lower surface.

In one embodiment, the multi-function sensor module includes a temperature contact point located at the lower surface, for directly contacting the object, the temperature contact point being coupled to the infrared temperature sensor module via a signal transmission structure.

In one embodiment, the infrared temperature sensor module includes an infrared sensor, a temperature sensing switch and a thermopile circuit, wherein when the temperature sensing switch receives a temperature signal higher than a predetermined threshold through the infrared sensor, the thermopile circuit is enabled to perform a real time temperature sensing function; and when the thermopile circuit is not enabled, the thermopile circuit is in a stand-by mode for saving power.

The objectives, technical details, features, and effects of the present invention will be better understood with regard to the detailed description of the embodiments below, with reference to the attached drawings.

DESCRIPTION OF THE PREFERRED EMBODIMENTS

The above and other technical details, features and effects of the present invention will be will be better understood with regard to the detailed description of the embodiments below, with reference to the drawings. The drawings as referred to throughout the description of the present invention are for illustration only, to show the interrelations between the apparatus and devices, but not drawn according to actual scale.

Figure 1A:
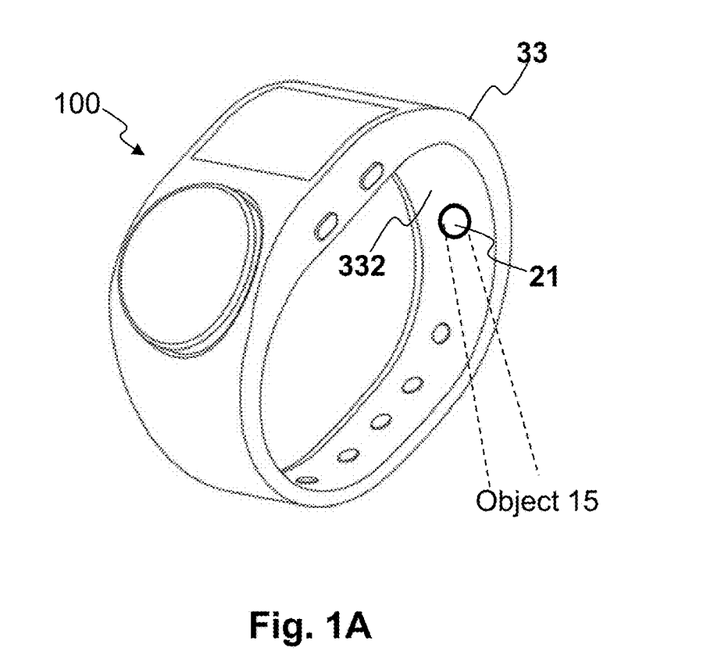
FIGS. 1A-1C are schematic views, showing several embodiments as to how a multi-function sensor module is provided inside a wearable assembly.
Figure 1B:
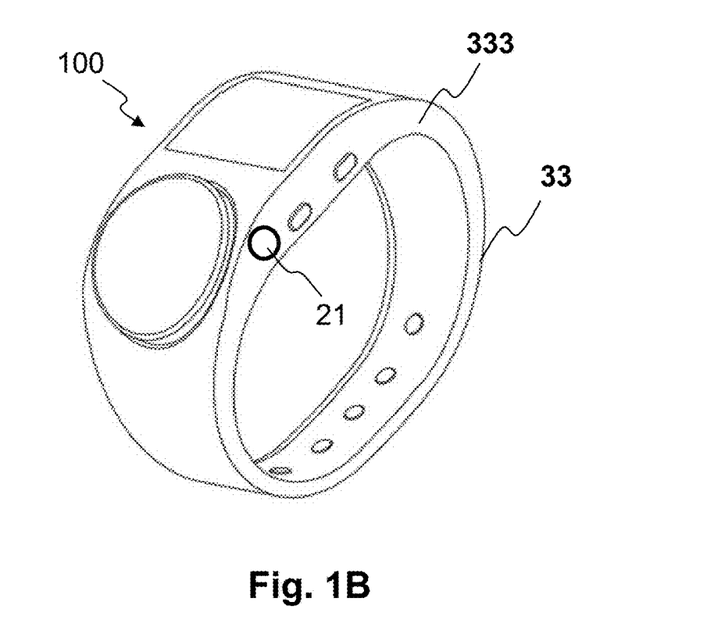
Figure 1C:
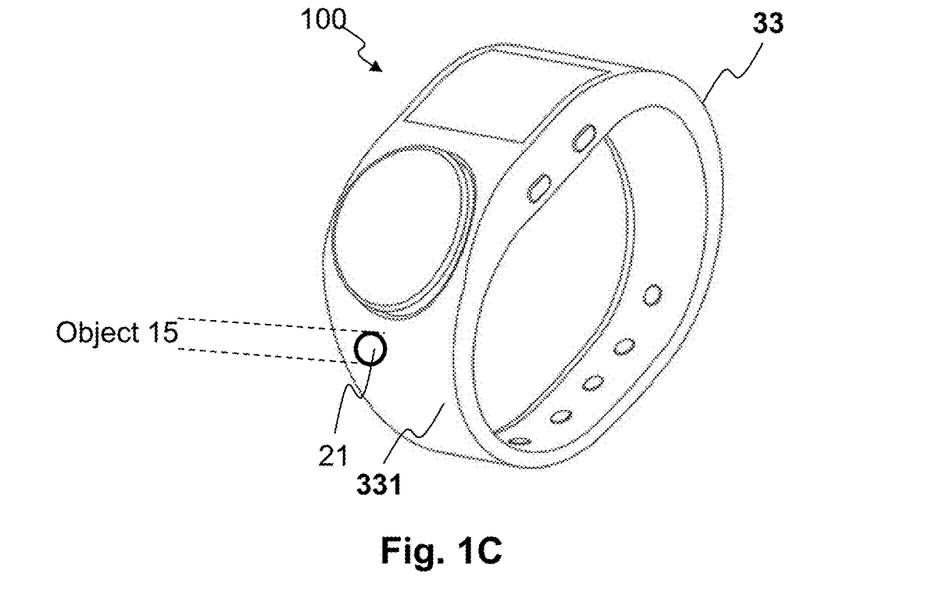
Figure 2A:
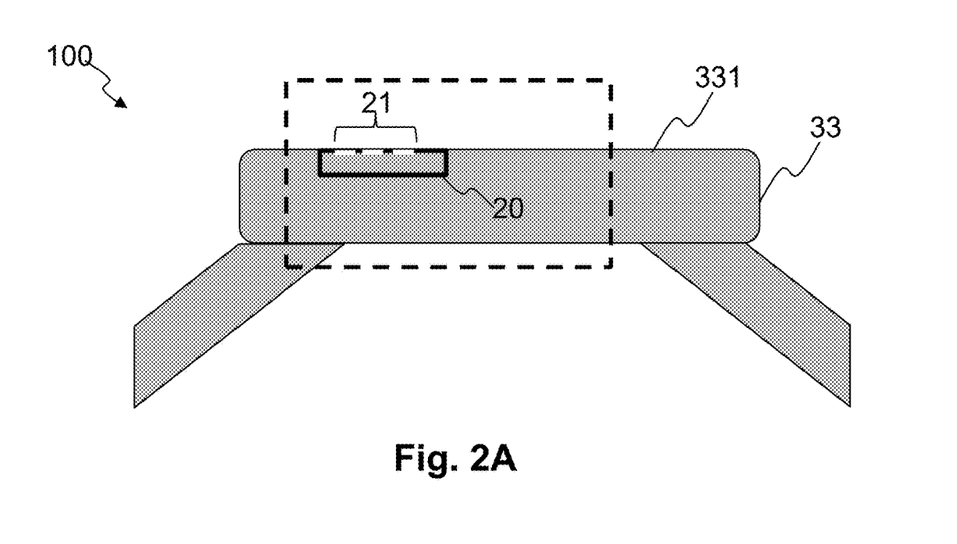
FIGS. 2A-2C are side views, showing several embodiments as to how a multi-function sensor module is provided inside a wearable assembly.
Figure 2B:
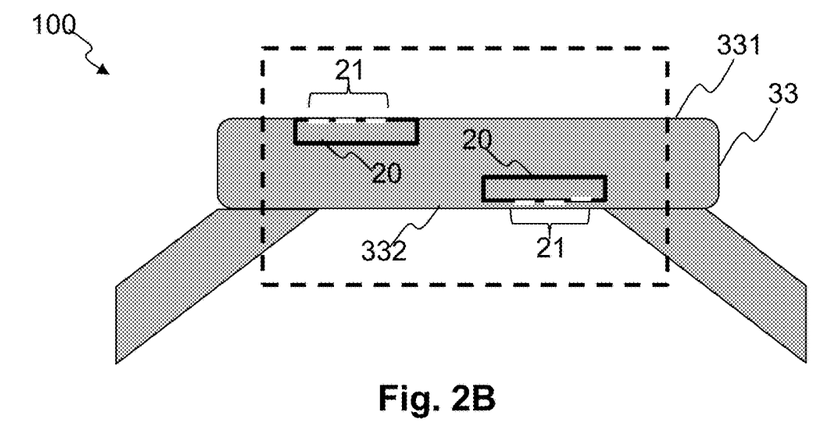
Figure 2C:
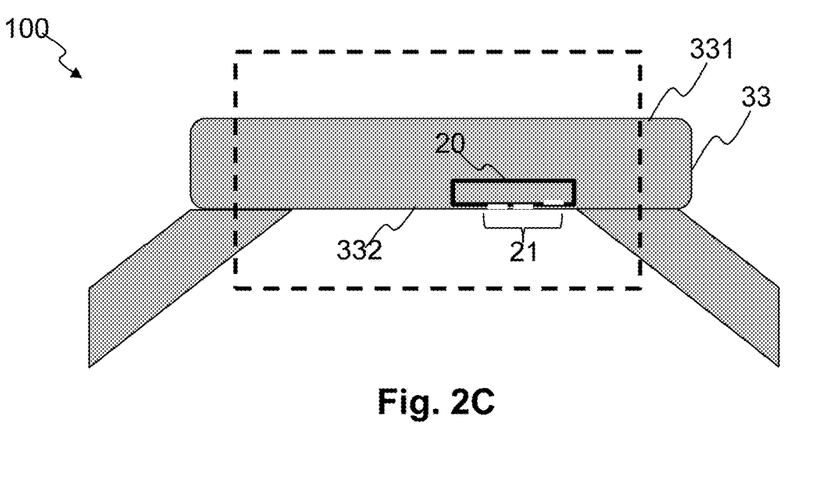

Please refer to FIGS. 1A-1C and FIGS. 2A-2C. FIGS. 1A-1C are schematic views, showing several embodiments as to how a multi-function sensor module is provided inside a wearable assembly. FIGS. 2A-2C are side views, showing several embodiments as to how a multi-function sensor module is provided inside a wearable assembly. As shown in FIG. 2A, a wearable device 100 with combined sensing capabilities includes a wearable assembly 33 and a multi-function sensor module 20 integrated inside the wearable assembly 33.

The wearable assembly 33 can be worn on a part of a user's body. In one embodiment, the wearable assembly 33 can be, for example but not limited to, a watch (which includes a watch body and watch strap). In other embodiments, the wearable assembly 33 can be any type of wearable product, or a belt or a metal chain for wearing.

The wearable assembly 33 has at least one light-transmissible window 21, which corresponds to one or more light-transmissible zones of the multi-function sensor module 20 (the term "corresponds to" as used in the above sentence is meant to indicate that a light beam passing through the light-transmissible window 21 can be transmitted to the one or more light-transmissible zones of the multi-function sensor module 20; however, there can be a distance between the light-transmissible window 21 and the one or more light-transmissible zones). FIG. 2A is a side view according to FIG. 1C. As shown in FIG. 1C and FIG. 2A, the light-transmissible window 21 is at an upper surface 331 of the wearable assembly 33. Thus, when an object 15 (for example but not limited to a finger or a wrist) is near the light-transmissible window 21 at the upper surface 331 of the wearable assembly 33, the multi-function sensor module 20 can sense the temperature of the finger or the wrist, for example in a non-contact manner. Certainly, the user also can put his finger, wrist or any other part to be sensed directly on and in contact with the light-transmissible window 21. (The structure and features as to how the multi-function sensor module 20 senses temperature will be described later.) In this embodiment, the multi-function sensor module 20 can further have, in addition to temperature sensing function, multiple other physical or biological feature sensing functions such as heart rate sensing function, blood pressure sensing function and/or blood oxygen concentration sensing function (to be described in detail later).

In this embodiment, because the multi-function sensor module 20 is located beneath the light-transmissible window 21 at the upper surface 331 of the wearable assembly 33, a user wearing the wearable device 100 with combined sensing capabilities can measure his or her forehead temperature by approaching his or her wrist near his or her forehead, or by approaching his or her body part to be measured near the light-transmissible window 21. In addition to measuring the user's own temperature, the wearable device 100 can also be used to measure the forehead (or other) temperature of any surrounding people, which does not require taking off the wearable assembly 33 from the user.

According to the present invention, the light-transmissible window 21 of the wearable assembly 33 can be located at, instead of or in addition to the upper surface 331 of the wearable assembly 33, a lower surface 332 of the wearable assembly 33 (as shown in FIG. 1A and FIG. 2C) and/or a lateral surface 333 of the wearable assembly 33 (as shown in FIG. 1B). The wearable assembly 33 can include one or more light-transmissible windows 21 depending on practical needs. The number and the location(s) of the multi-function sensor module 20 can be correspondingly arranged according to the number and the location(s) of the light-transmissible window 21.

FIG. 2C is a side view according to FIG. 1A. As shown in FIG. 1A and FIG. 2C, the light-transmissible window 21 is located at a lower surface 332 of the wearable assembly 33. Thus, when the user wears the wearable assembly 33 (for example but not limited to a watch) on his or her wrist, the light-transmissible window 21 at the lower surface 332 of the wearable assembly 33 will be facing the object 15 (for example but not limited to the skin of the wrist). As such, the multi-function sensor module 20 can sense the temperature of the skin of the wrist, for example by direct contact. In this embodiment, the wearable device 100 with combined sensing capabilities can perform biological feature monitoring functions such as physical strength evaluation during exercise, body temperature recording, skin temperature monitoring (sun-burnt monitoring), abnormal temperature alarming and energy consumption evaluation, etc. (The details as to how the multi-function sensor module 20 senses temperature will be described later).

When the temperature or other physiological information is sensed by direct contact, the light-transmissible window 21 of the wearable assembly 33 can be implemented as an aperture. On the other hand, when the temperature or other physiological information is sensed by a non-contact manner, the light-transmissible window 21 of the wearable assembly 33 can be implemented as an aperture or a window made of a light-transmissible material.

In one embodiment, the number of the multi-function sensor module 20 is not limited to one, but can be plural as necessary. For example, as shown in FIG. 2B, the wearable device 100 with combined sensing capabilities can include one wearable assembly 33 and two multi-function sensor modules integrated into the wearable assembly 33. One light-transmissible window 21 is provided at an upper surface 331 of the wearable assembly 33, corresponding to one of the two multi-function sensor modules 20, while another light-transmissible window 21 is provided at a lower surface 332 of the wearable assembly 33, corresponding to another one of the two multi-function sensor modules 20. Thus, in the embodiment shown in FIG. 2B, both "non-contact type temperature sensing" (through the light-transmissible window 21 at the upper surface 331) and "contact type temperature sensing" (through the light-transmissible window 21 at the lower surface 332) are integrated into one single wearable assembly 33.

In other embodiments, the number of the multi-function sensor module 20 is not limited to two (as shown in FIG. 2B), but can be more as necessary. In other words, two or more light-transmissible windows 21 can be provided at the wearable assembly 33 at two or more of the upper surface 331, the lower surface 332 and the lateral surface 333 of the wearable assembly 33 (i.e., any combination of two or more of FIGS. 1A to 1C).

Figure 3:
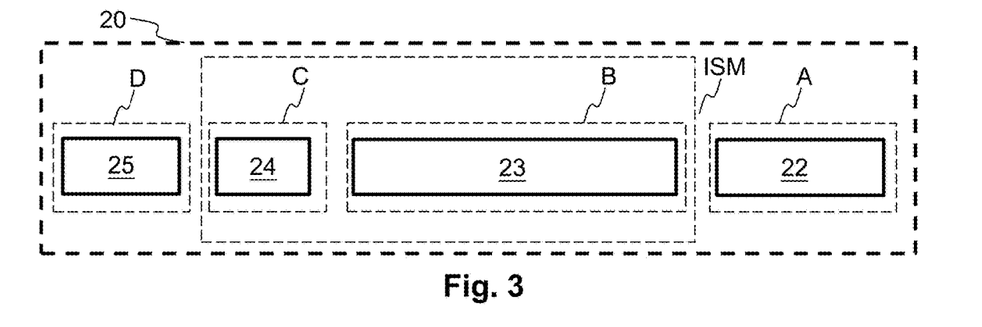
FIG. 3 shows a top view of a multi-function sensor module according to an embodiment of the present invention.
Figure 5A:
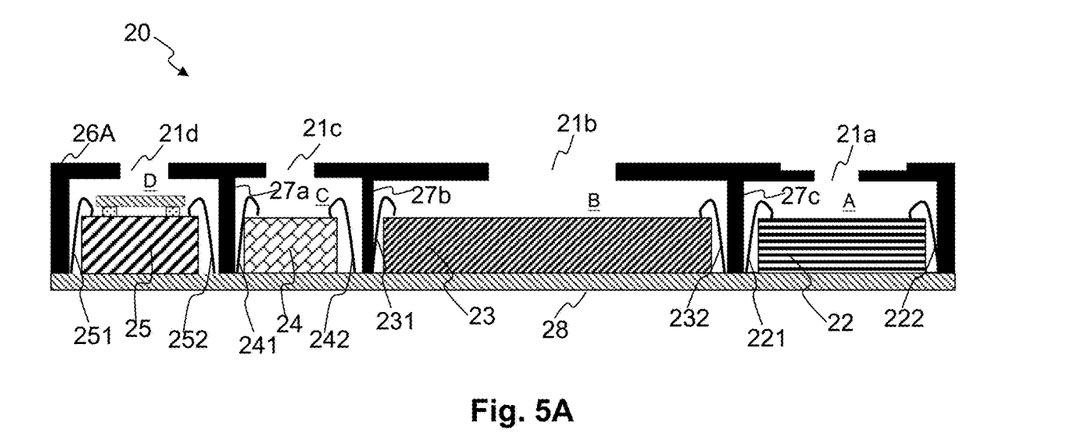
FIGS. 5A-5C show several embodiments of the multi-function sensor module of the present invention.

Please refer to FIG. 3 in conjugation with FIG. 5. FIG. 3 shows a top view of a multi-function sensor module according to an embodiment of the present invention. FIG. 5A shows a cross sectional view of the multi-function sensor module of the present invention. The multi-function sensor module 20 at least includes: a chip or a module for sensing a physical or a biological feature of an object by way of image sensing (hereinafter referred to as "image sensor module" regardless whether it is a chip or a module) and a chip or a module for sensing temperature of the object by way of infrared temperature sensing (hereinafter referred to as "infrared temperature sensor module" regardless whether it is a chip or a module). Sensing a physical or a biological feature of an object by way of image sensing for example can be, but not limited to, sensing heart rate, blood oxygen concentration, blood pressure, breathing rate, and so on. Sensing temperature of the object by way of infrared temperature sensing for example can be, but not limited to, sensing human body temperature. Or, in another embodiment, a thermal image of the object can be sensed by way of infrared temperature sensing. In addition, the multi-function sensor module 20 can further include a chip or a module with another function such as, but not limited to, a sweat sensor, an ultraviolet light sensor, a gas sensor, an accelerometer, a gyroscope, an altimeter and/or a pedometer. The term "image sensor module" as described herein is meant to indicate a sensor module which generates information according to changes between images (e.g., for generating information of heart rate, blood oxygen concentration, blood pressure and/or breathing rate according to changes between images). The term "infrared temperature sensor module" as described herein is meant to indicate a sensor module for sensing temperature according to infrared information (for example but not limited to sensing body temperature).

In one embodiment, the image sensor module includes a light source and an image sensor. For better performance, it is preferred to isolate the light source from the image sensor, so that a light beam emitted from the light source will only be reflected by the object but will not be transmitted to the image sensor directly. In this case, the light source and the image sensor can be disposed at two different chambers. With respect to the other chips or modules of the multi-function sensor module 20, they can be disposed at another chamber or other chambers. Some of the chips or modules can share a same chamber as long as their signals will not interfere one another. In other words, according to the present invention, the multi-function sensor module 20 at least includes an image sensor module and an infrared temperature sensor module, while the number of the chambers can be determined depending on practical needs. The chambers can be entirely or partially compartmented.

FIG. 5A shows a cross sectional view of the multi-function sensor module 20 of the present invention. As shown in FIG. 5A, in this embodiment, the multi-function sensor module 20 includes a substrate 28. A first chamber A, a second chamber B, a third chamber C and a fourth chamber D are formed on the substrate 28 through partitioning members 27a, 27b, and 27c. A cap 26A is covered on the top and the peripheral sides of the chambers.

Still referring to FIG. 3 and FIG. 5A, the multi-function sensor module 20 of this embodiment includes an infrared temperature sensor module 22 and an image sensor module ISM. The image sensor module ISM includes a light source 24 and an image sensor 23. The light source 24 for example can be, but is not limited to, a light emitting diode device. The image sensor 23 for example can be, but is not limited to, a heart rate sensor. The light emitting diode device provides a light beam (for example but not limited to a visible light), which is reflected by an object (e.g., a human body), and then transmitted to the heart rate sensor, for sensing the heart rate. The same approach can be adopted to sensing blood oxygen concentration, blood pressure and/or breathing rate. As a more specific example, if it is desired to sense heart rate, the light source 24 can be a green light source. The image sensor 23 receives the light beam reflected by the object, and analyzes the reflected light beam to obtain the heart rate information. Certainly, to measure different biological features, the light source 24 and the image sensor 23 can be arranged otherwise, to cooperate with each other. The above-mentioned embodiment is for illustrative purpose only, but not for limiting the scope of the present invention.

Figure 9A:
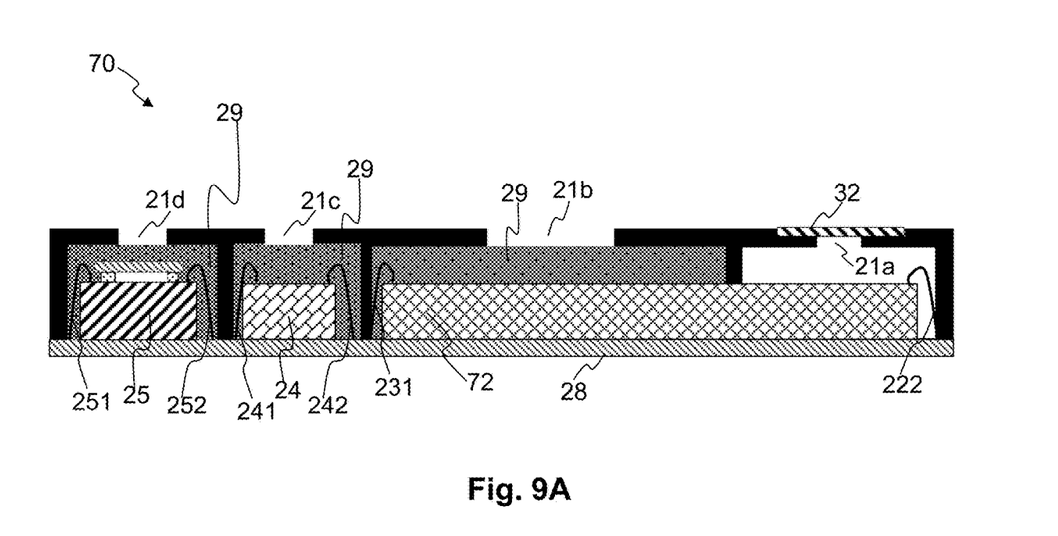
FIGS. 9A-9C show several further other embodiments of the multi-function sensor module of the present invention.

The multi-function sensor module 20 can further include, in addition to the infrared temperature sensor module 22, the image sensor module 23 and the light source 24, a device for performing another function, such as a Micro-electro-mechanical Systems (MEMS) device 25. The MEMS device 25 can be, for example but not limited to, a sweat sensor, an ultraviolet light sensor, a gas sensor, an accelerometer, a gyroscope, an altimeter or a pedometer. The infrared temperature sensor module 22, the image sensor module 23, the light source 24 and the MEMS device 25 are accommodated into the above-mentioned first chamber A, second chamber B, third chamber C and fourth chamber D, respectively. Note that the relative positions of the chambers are not limited to the arrangement shown in the figure, but can be arranged otherwise. If it is required to incorporate more than two MEMS devices 25, the number of the chambers can be increased. Also, if some of the modules do not need to be isolated form one another, the number of the chambers can be reduced (e.g., referring to the embodiment shown in FIG. 9, which will be described later). Besides, if the MEMS device 25 is a type of sensor such as an accelerometer, an ultraviolet light sensor, a gyroscope, an altimeter or a pedometer, it is not necessary to form an aperture at a corresponding position above the MEMS device 25. On the other hand, if the MEMS device 25 is a type of sensor such as a sweat sensor and a gas sensor, it will be necessary to form an aperture at a corresponding position above the MEMS device 25. FIGS. 5A-5D are for illustrative purpose only, but not for limiting the scope of the present invention.

One of the features of the present invention is that: the wearable device 100 with combined sensing capabilities integrates heart rate sensing function and temperature sensing function in one device, so that the wearable device 100 is more convenient and friendly to a user, and the volume as well as the manufacturing cost of the device is reduced.

Figure 4:
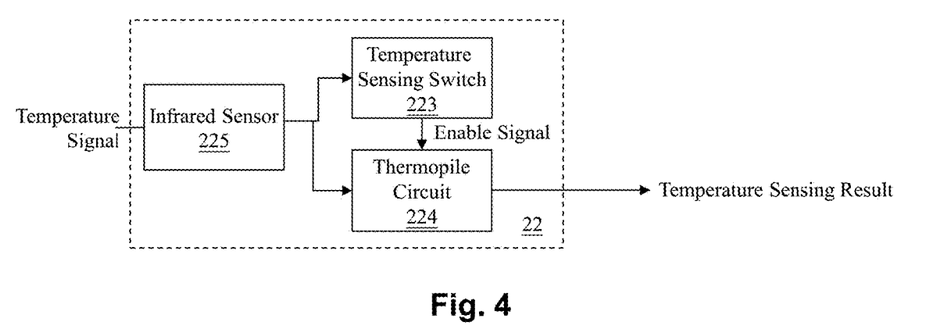
FIG. 4 shows a block diagram as to how the present invention performs a real time temperature sensing function.

In one embodiment, the infrared temperature sensor module 22 can be a thermopile temperature sensor module, which is manufactured through a standard CMOS process. In one example, a thermopile temperature sensor module includes P-type materials and N-type materials connected in series, which generates a change in voltage in response to a change in temperature. Referring to FIG. 4 for a more specific embodiment, the infrared temperature sensor module 22 can include an infrared sensor 225, a temperature sensing switch 223 and a thermopile circuit 224. When the temperature sensing switch 223 receives a temperature signal higher than a predetermined threshold through the infrared sensor 225 (regardless whether it senses temperature by the "contact type" shown in FIG. 1A or the "non-contact type" shown in FIG. 1C), the temperature sensing switch 223 enables the thermopile circuit 224 to perform a real time temperature sensing function; when the thermopile circuit 224 is not enabled, the thermopile circuit 224 is in a stand-by mode to save power.

In one embodiment, the infrared temperature sensor module 22 can sense temperature in a "non-contact" manner. For example, when the user wears on the wearable assembly 33 (for example but not limited to a watch), the wearable assembly 33 can sense temperature in a non-contact manner as shown in FIG. 1C, and can simultaneously sense the user's heart rate. More specifically, the wavelength detected by the infrared temperature sensor module 22 employing a thermopile is usually in a far infrared wavelength range. That is, temperature of an object can be sensed by detecting the far infrared ray emitted from that object. Therefore, if the wavelengths to be detected by the infrared temperature sensor module 22 and the image sensor 23 are different from each other, it is not necessary to isolate them from each other.

In another embodiment, the infrared temperature sensor module 22 can sense temperature byway of direct contact. Under such circumstance, when the user wears the wearable assembly 33 (for example but not limited to a watch) on his or her wrist, the wearable assembly 33 can sense temperature in a direct contact manner as shown in FIG. 1A, and can simultaneously sense the user's heart rate.

Still referring to FIG. 5A, the multi-function sensor module 20 includes a first light-transmissible zone 21a, a second light-transmissible zone 21b, a third light-transmissible zone 21c and a fourth light-transmissible zone 21d. The first light-transmissible zone 21a corresponds to the infrared temperature sensor module 22 in the first chamber A; the second light-transmissible zone 21b corresponds to the image sensor 23 in the second chamber B; the third light-transmissible zone 21c corresponds to the light source 24 in the third chamber C; the fourth light-transmissible zone 21d corresponds to the MEMS device 25 in the fourth chamber D. The infrared temperature sensor module 22 is electrically connected to a corresponding external circuit via conduction wires 221 and 222. The image sensor 23 is electrically connected to a corresponding external circuit via conduction wires 231 and 232. The light source 24 is electrically connected to a corresponding external circuit via conduction wires 241 and 242. The MEMS device 25 is electrically connected to a corresponding external circuit via conduction wires 251 and 252. A light beam is allowed to transmit between each of the light-transmissible zones 21a-21d and the light-transmissible window 21 (referring to FIGS. 2A-2C), respectively (i.e., a light beam can be transmitted between each light-transmissible zone and the light-transmissible window 21, but preferably not between two light-transmissible zones).

In one embodiment, in the multi-function sensor module 20 shown in FIG. 5A, the first chamber A, the second chamber B and the third chamber C are not filled with any filler material, and the fourth chamber D is also not filled with any filler material, as the multi-function sensor module 20 is packaged.

In another embodiment, the fourth chamber D may not require the fourth light-transmissible zone 21d. Under such situation, in one embodiment, the cap 26A can be made of a transparent material. More specifically, on one hand, when it is required to transmit or receive light in a chamber, it is necessary for this chamber to have a light-transmissible zone or employ a transparent material as its cap. For example, it is necessary for the chambers wherein the light source, the image sensor and the infrared temperature sensor module are accommodated to be able to transmit or receive light, so these chambers require a light-transmissible zone or a transparent cap. On the other hand, when it is not required to transmit or receive light in a chamber, it is not necessary for this chamber to be light-transmissible. For example, it is not necessary for the chamber wherein an accelerator is accommodated to be light-transmissible, and thus a light-transmissible zone or a transparent cap is not required for this chamber. The chambers in the present invention can be designed according to the above-mentioned principles.

For the sake of simplicity, in the following FIGS. 5B-5C, the numerical references assigned to the first chamber A, the second chamber B, the third chamber C, the fourth chamber D, the cap 26A and the partitioning members 27a, 27b and 27c will not be shown. Please refer to FIGS. 5B-5C in conjugation with FIG. 5A.

Figure 5B:
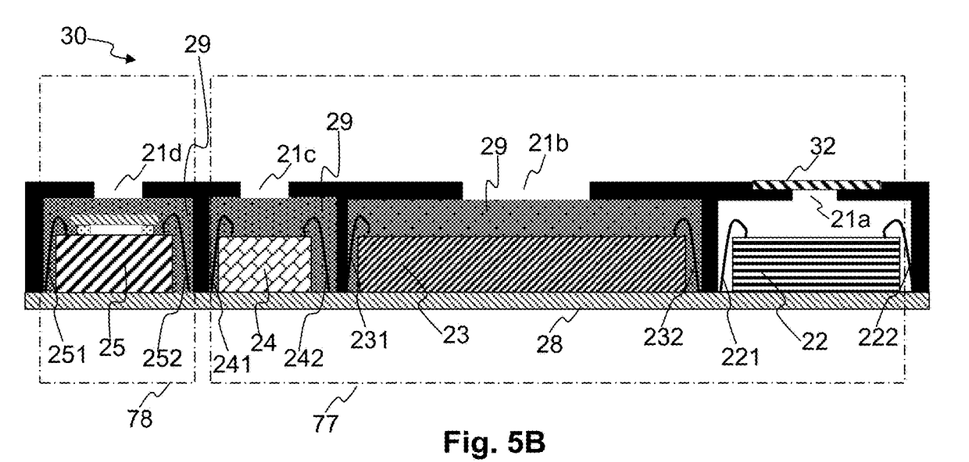

Please refer to FIG. 5B, which shows another embodiment of the multi-function sensor module of the present invention. The multi-function sensor module 30 of this embodiment is similar to the multi-function sensor module 20 of the previous embodiment, but is different in that: in the multi-function sensor module 30 of this embodiment, the second chamber B and the third chamber C are filled with a filler material 29 as the multi-function sensor module 30 is packaged, such that the chips or the modules in the chambers are fully covered with or at least partially covered with the filler material 29, whereas the multi-function sensor module 20 of the above-mentioned embodiment does not include any filler material in any chamber. The filler material 29 for example can be, but not limited to, a waterproof sealing material, a transparent material, or any other type of filler material. The fourth chamber D can also be filled with a filler material 29 as the multi-function sensor module 30 is packaged. This filler material 29 for example can be, but not limited to, a waterproof sealing material, a transparent material, a transparent material incorporating melanin for light shielding effect, or any other type of filler material. In one embodiment, the filler material 29 filled in the second chamber B, the third chamber C and the fourth chamber D is a same material (as shown in FIG. 5B). In another embodiment, the filler materials 29 filled in the second chamber B, the third chamber C and the fourth chamber D are different from one another. The filler material 29 can be used to, for example but not limited to, filter light and/or prevent unwanted dusts from entering into the chambers.

In the embodiment shown in FIG. 5B, preferably, a filtering material 32 can be adopted to entirely or partially seal the first light-transmissible zone 21a of the first chamber A. The filtering material 32 can filter signals other than the infrared range, such that the infrared temperature sensor module 22 can receive the infrared temperature signal more accurately, to increase the sensitivity of the infrared temperature sensor module 22. In one embodiment, the filtering material 32 for example can be, but not limited to, a transparent material incorporating melanin for light shielding effect. Besides, as mentioned above, it may not be required for the fourth chamber D to include the fourth light-transmissible zone 21d, and the cap 26A for example can be made of a transparent material; or, if it is not required for the device in the fourth chamber D to transmit or receive light, the fourth chamber D does not need to be light-transmissible.

Figure 5C:
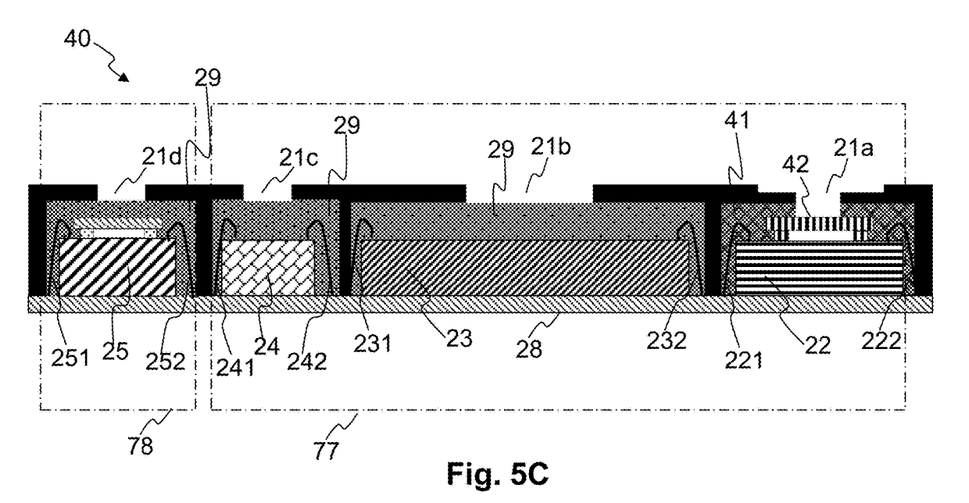
Figure 6A:
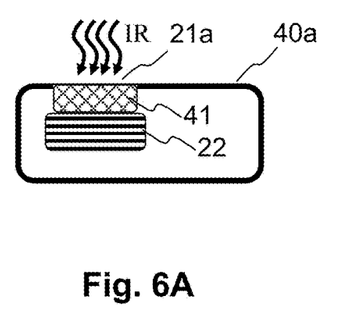
FIGS. 6A-6D show several other embodiments of the multi-function sensor module of the present invention.
Figure 6B:
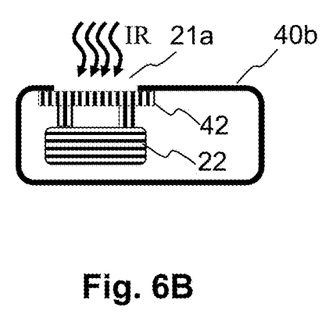
Figure 6C:
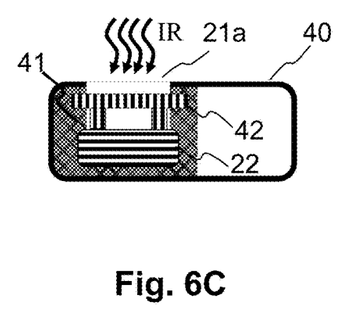

Please refer to FIG. 5C in conjugation with FIG. 6C. FIG. 5C shows another embodiment of the multi-function sensor module of the present invention. FIG. 6C is a simplified schematic diagram according to FIG. 5C. For the sake of simplicity, only the infrared temperature sensor module 22 is illustrated in FIG. 6C.

The multi-function sensor module 40 of this embodiment is similar to the multi-function sensor module 30 of the above-mentioned embodiment, but is different in that:

First, in the multi-function sensor module 40 of this embodiment, the first chamber A is filled with a protection material 41 as the multi-function sensor module 40 is packaged. In one embodiment, the protection material 41 for example can be, but not limited to, polyethylene (PE), polypropylene/polypropene (PP), polyethylene terephthalate (PET) or any other infrared light transmissible material.

Second, the first chamber A further includes a protection cap layer 42 located above the infrared temperature sensor module 22. The protection cap layer 42 only allows an infrared temperature signal, which for example is generated from the object (such as the finger 15 shown in FIG. 1A), to pass through. In one embodiment, the protection cap layer 42 for example is made of, but not limited to, polyethylene (PE), polypropylene/polypropene (PP), polyethylene terephthalate (PET) or any other infrared light transmissible material. The protection material 41 as well as the protection cap layer 42 can be used to, for example but not limited to, filter light and/or prevent unwanted dusts from entering into the infrared temperature sensor module 22. As mentioned above, in another embodiment, it may not be required for the fourth chamber D to include the fourth light-transmissible zone 21d, and the cap 26A for example can be made of a transparent material; or, if it is not required for the device in the fourth chamber D to transmit or receive light, the fourth chamber D does not need to be light-transmissible.

Please refer to FIG. 6A. FIG. 6A shows another embodiment of the multi-function sensor module of the present invention. For the sake of simplicity, only the infrared temperature sensor module 22 is illustrated in FIG. 6A. Please refer to FIG. 5C in conjugation with FIG. 6A.

The multi-function sensor module 40a of this embodiment is similar to the multi-function sensor module 40 of the above-mentioned embodiment, but is different in that: first, the first light-transmissible zone 21a is directly sealed with a protection material 41; second, the first chamber A in the multi-function sensor module 40a does not include a protection cap layer 42. Similar to the previous embodiment, the protection material 41 can be used to, for example but not limited to, filter light and/or prevent unwanted dusts from entering into the infrared temperature sensor module 22.

Please refer to FIG. 6B. FIG. 6B shows another embodiment of the multi-function sensor module of the present invention. For the sake of simplicity, only the infrared temperature sensor module 22 is illustrated in FIG. 6B. Please refer to FIG. 5C in conjugation with FIG. 6B.

The multi-function sensor module 40b of this embodiment is similar to the multi-function sensor module 40 of the above-mentioned embodiment, but is different in that: first, the first chamber A is not filled with a protection material 41 as the multi-function sensor module 40b is packaged; second, only the protection cap layer 42 is provided for protecting the infrared temperature sensor module 22. Similar to the above-mentioned embodiments, the protection cap layer 42 can be used to, for example but not limited to, filter light and/or prevent unwanted dusts from entering into the infrared temperature sensor module 22.

Figure 6D:
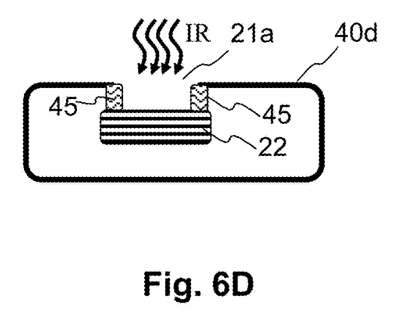

Please refer to FIG. 6D. FIG. 6D shows another embodiment of the multi-function sensor module of the present invention. For the sake of simplicity, only the infrared temperature sensor module 22 is illustrated in FIG. 6D. Please refer to FIG. 5C in conjugation with FIG. 6D.

The multi-function sensor module 40d of this embodiment is similar to the multi-function sensor module 40 of the above-mentioned embodiment, but is different in that: first, the first chamber A is not filled with a protection material 41 as the multi-function sensor module 40d is packaged; second, this embodiment does not include a protection cap layer 42. Instead, a protection ring 45 is provided at the periphery of a space between the infrared temperature sensor module 22 and the first light-transmissible zone 21a. The protection ring 45 prevents unwanted dusts from entering into the first chamber A through the periphery of the space between the infrared temperature sensor module 22 and the first light-transmissible zone 21a. The protection ring 45 can be made of any material, as long as such material can seal the periphery of the space between the infrared temperature sensor module 22 and the first light-transmissible zone 21a.

Figure 7A:
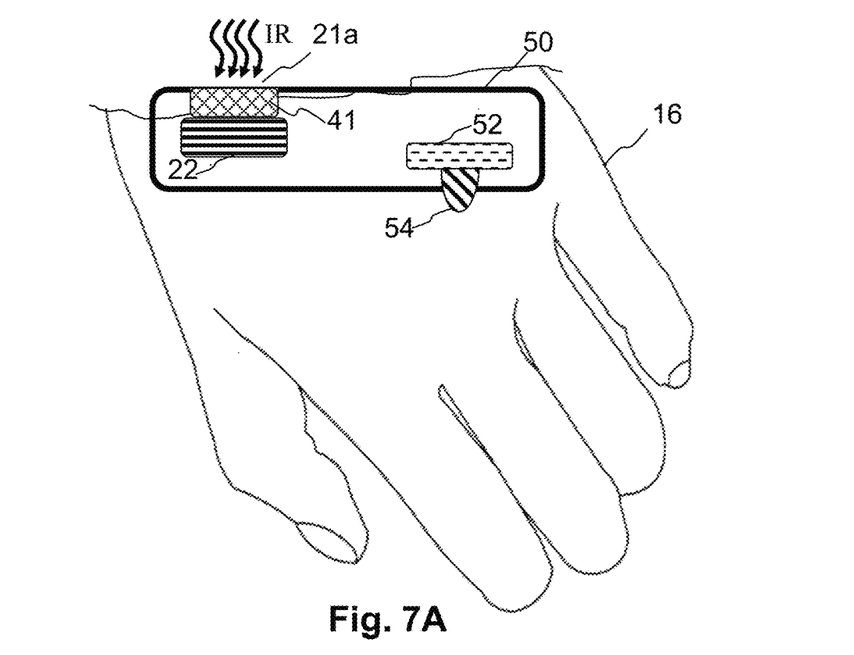
FIGS. 7A-7B show several further other embodiments of the multi-function sensor module of the present invention.

Please refer to FIG. 7A. FIG. 7A shows a further other embodiment of the multi-function sensor module of the present invention. In the embodiment shown in FIG. 7A, the present invention integrates "contact type temperature sensing function" and "non-contact type temperature sensing function" into one single multi-function sensor module 50.

For the sake of simplicity, only the infrared temperature sensor module 22 is illustrated in FIG. 7A, while the other parts are omitted.

In this embodiment, the multi-function sensor module 50 further includes a contact type temperature sensor 52 and a temperature contact point 54. In this embodiment, when a user wears the wearable assembly 33 (for example but not limited to a watch) on his or her wrist, the temperature contact point 54 of the wearable assembly 33 will be facing the object 16 directly (for example but not limited to the skin of the wrist). Thus, the multi-function sensor module 50 of this embodiment can sense the temperature of the skin of the wrist by the contact type temperature sensor 52. The temperature contact point 54 directly contacts the object 16; the contact type temperature sensor 52 determines the temperature according to the signal transmitted from the temperature contact point 54. The temperature contact point 54 and the light-transmissible window 21 (referring to FIGS. 2A-2C) are at different sides of the multi-function sensor module 50. The multi-function sensor module 50 can sense a forehead temperature in a non-contact manner through the light-transmissible window 21 (and the first light-transmissible zone 21*a*)

That is, in this embodiment, the user not only can sense the skin temperature of the wrist by direct contact (which for example can be used to trace a change in a user's body temperature), but also can sense a temperature in a non-contact manner (which for example can be used to sense the temperature of other people or objects nearby), whereby the wearable device 100 with combined sensing capabilities of the present invention is more friendly and convenient to a user.

Besides the above, the multi-function sensor module 50 of this embodiment also has the same advantages and features as the above-mentioned multi-function sensor modules 20, 30 and 40, which are not redundantly repeated here.

Figure 7B:
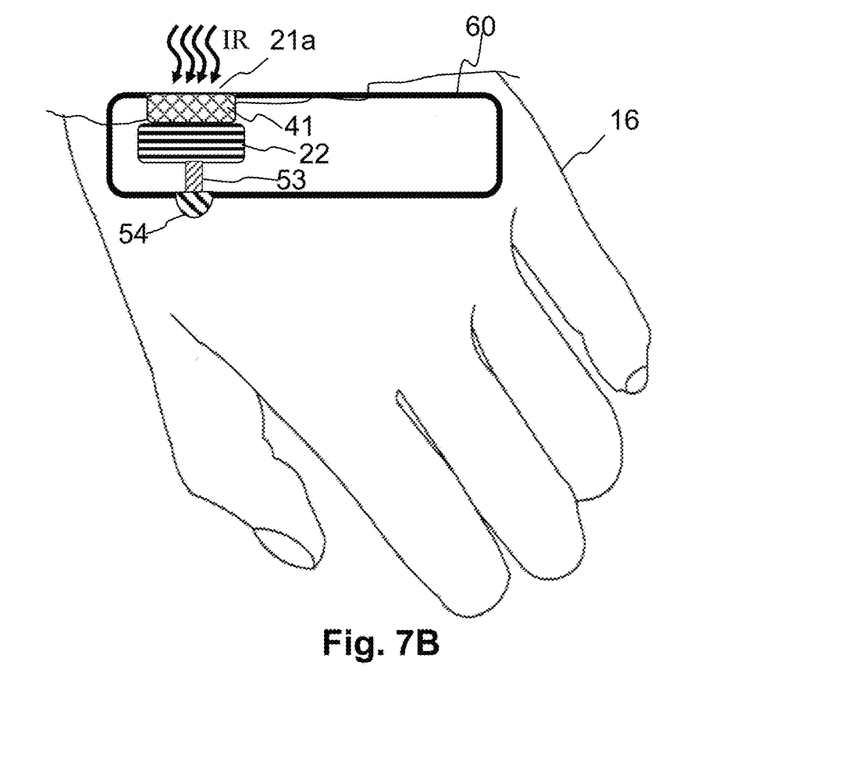

Please refer to FIG. 7B. FIG. 7B shows another embodiment of the multi-function sensor module of the present invention. For the sake of simplicity, only the infrared temperature sensor module 22 is illustrated in FIG. 7B.

The multi-function sensor module 60 of this embodiment is similar to the multi-function sensor module 50 of the above-mentioned embodiment, but is different in that: the temperature contact point 54 is coupled to the infrared temperature sensor module 22 via a signal transmission structure 53. Hence, only one single infrared temperature sensor module 22 is required to sense the temperature and generate the temperature readout.

Besides the above, the multi-function sensor module 60 of this embodiment also has the same advantages and features as the above-mentioned multi-function sensor modules 20, 30, 40 and 50, which are not redundantly repeated here.

Figure 8:
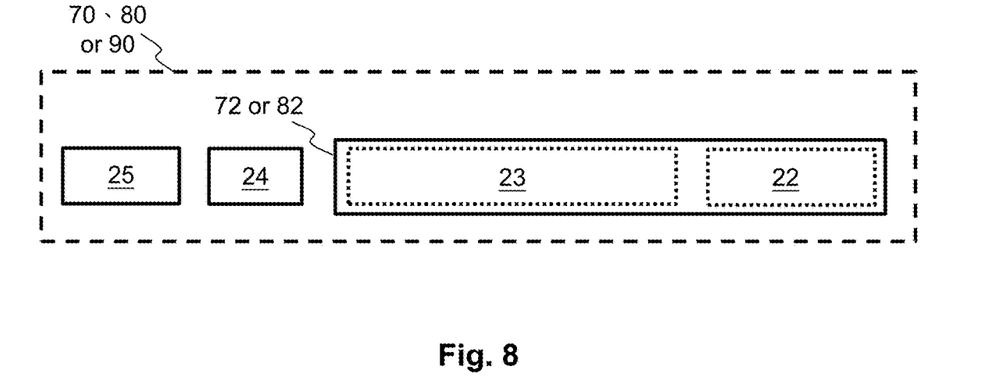
FIG. 8 shows a top view of a multi-function sensor module according to another embodiment of the present invention.

Please refer to FIG. 8 in conjugation with FIG. 9A. FIG. 8 shows a top view of a multi-function sensor module according to another embodiment of the present invention. FIG. 9A shows a cross-sectional view of another embodiment of the multi-function sensor module of the present invention.

The multi-function sensor module 70 of this embodiment is similar to the multi-function sensor module 30 of the above-mentioned embodiment, but is different in that: the infrared temperature sensor module 22 and the image sensor module 23 shown in FIG. 5B is integrated as one single image sensor-infrared temperature sensor complex module 72 (as shown by the top view of FIG. 8), so that the volume and the manufacturing cost of the product are effectively reduced. The image sensor-infrared temperature sensor complex module 72 is electrically connected to a corresponding external circuit via conduction wires 231 and 232.

Besides the above, the multi-function sensor module 70 of this embodiment also has the same advantages and features as the above-mentioned multi-function sensor module 30, which are not redundantly repeated here.

Figure 9B:
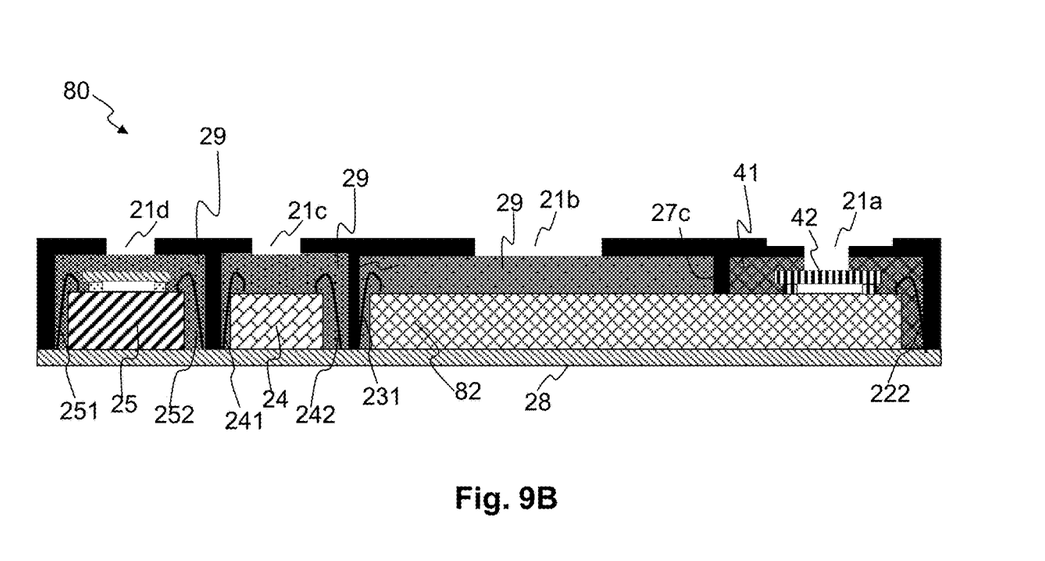

Please refer to FIG. 9B, which shows another embodiment of the multi-function sensor module of the present invention. The multi-function sensor module 80 of this embodiment is similar to the multi-function sensor module 40 of the above-mentioned embodiment, but is different in that: the infrared temperature sensor module 22 and the image sensor module 23 shown in FIG. 5C is integrated as one single image sensor-infrared temperature sensor complex module 82 (as shown by the top view of FIG. 8), so that the volume and the manufacturing cost of the product are effectively reduced.

Besides the above, the multi-function sensor module 80 of this embodiment also has the same advantages and features as the above-mentioned multi-function sensor module 40, which are not redundantly repeated here.

Figure 9C:
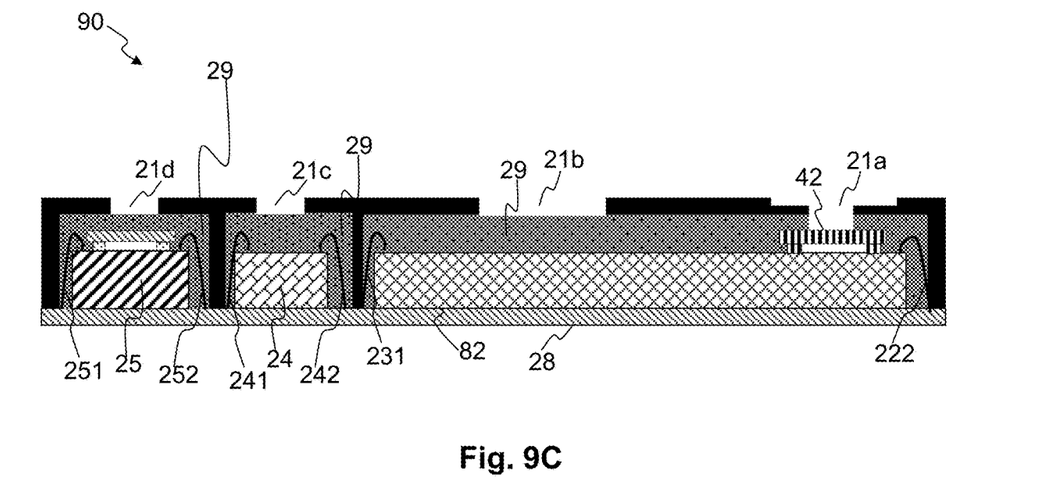

Please refer to FIG. 9C, which shows a further other embodiment of the multi-function sensor module of the present invention. The multi-function sensor module 90 of this embodiment is similar to the multi-function sensor module 80 of the above-mentioned embodiment, but is different in that: as compared to the image sensor-infrared temperature sensor complex module 82 shown in FIG. 9C, which employs a partitioning member 27*c* to separate the first chamber A and the second chamber B, the multi-function sensor module 90 of this embodiment merges the first chamber A and the second chamber B to become one single chamber, so there is no longer a partitioning member 27*c* in the multi-function sensor module 90. In the embodiment shown in FIG. 9C, the chamber wherein the image sensor-infrared temperature sensor complex module 82 is accommodated can be filled with the above-mentioned filler material 29 as the multi-function sensor module 90 is packaged.

The present invention has been described in considerable detail with reference to certain preferred embodiments thereof. It should be understood that the description is for illustrative purpose, not for limiting the scope of the present invention. An embodiment or a claim of the present invention does not need to achieve all the objectives or advantages of the present invention. The title and abstract are provided for assisting searches but not for limiting the scope of the present invention. Those skilled in this art can readily conceive variations and modifications within the spirit of the present invention. In view of the foregoing, the spirit of the present invention should cover all such and other modifications and variations, which should be interpreted to fall within the scope of the following claims and their equivalents.

What is claimed is:

1. A wearable device with combined sensing capabilities, comprising:
    a wearable assembly for being worn on a part of a user's body, wherein the wearable assembly has at least two light-transmissible windows, one of the at least two light-transmissible windows is provided at an upper surface of the wearable assembly, and another one of the at least two light-transmissible windows is provided at a lower surface of the wearable assembly; and at least two multi-function sensor modules located inside the wearable assembly, wherein, the at least two multi-function sensor modules are respectively corresponding to the two light-transmissible windows, wherein, the at least two multi-function sensor modules are for performing an image sensing function and an infrared temperature sensing function, each of the at least two multi-function sensor modules including:
an image sensor module for sensing a physical or a biological feature of an object through the at least one light-transmissible window by way of image sensing; and
an infrared temperature sensor module for sensing temperature through the corresponding light-transmissible window by way of infrared temperature sensing;
wherein, the multi-function sensor module corresponding to the light-transmissible window provided at the upper surface performs non-contact type temperature sensing through the corresponding light-transmissible window at the upper surface, and wherein the multi-function sensor module corresponding to the light-transmissible window provided at the lower surface performs contact type temperature sensing through the corresponding light-transmissible window at the lower surface;
whereby, the wearable device integrates both non-contact type temperature sensing and contact type temperature sensing into the one single wearable assembly.

2. The wearable device with combined sensing capabilities of claim 1, wherein the image sensor module is for sensing heart rate, blood oxygen concentration, blood pressure or breathing rate.

3. A wearable device with combined sensing capabilities, comprising:
a wearable assembly for being worn on a part of a user's body, wherein the wearable assembly has a light-transmissible window at an upper surface of the wearable assembly; and
at least one multi-function sensor module located inside the wearable assembly, for performing an image sensing function and an infrared temperature sensing function, the multi-function sensor module including:
an image sensor module for sensing a physical or a biological feature of an object through at least one of the light-transmissible windows by way of image sensing;
an infrared temperature sensor module for sensing temperature through the light-transmissible window by way of infrared temperature sensing; and
a contact type temperature sensor, for sensing temperature a temperature contact point located at the lower surface, for directly contacting the object, the temperature contact point being coupled to the contact type temperature sensor;
wherein, the temperature contact point located at the lower surface and the light-transmissible window located at the upper surface are at different sides of the multi-function sensor module;
wherein, the multi-function sensor module performs non-contact type temperature sensing through the light-transmissible window at the upper surface and performs contact type temperature sensing through the temperature contact point at the lower surface;
whereby, the wearable device integrates both non-contact type temperature sensing and contact type temperature sensing into one single wearable assembly.

* * * * *